United States Patent [19]
Naser et al.

[11] Patent Number: 4,878,488
[45] Date of Patent: Nov. 7, 1989

[54] SHOCK WAVE TUBE WITH LONG SERVICE LIFE

[75] Inventors: Georg Naser, Zirndorf; Helmut Reichenberger, Eckental; Karl-Heinz Schlee, Neunkirchen, all of Fed. Rep. of Germany

[73] Assignee: Siemens Aktiengesellschaft, Berlin and Munich, Fed. Rep. of Germany

[21] Appl. No.: 170,584

[22] Filed: Mar. 17, 1988

Related U.S. Application Data

[63] Continuation of Ser. No. 821,085, Jan. 21, 1986, abandoned.

[30] Foreign Application Priority Data

Jan. 28, 1985 [DE] Fed. Rep. of Germany ....... 3502751

[51] Int. Cl.[4] .............................................. A61B 17/22
[52] U.S. Cl. .................................. 128/24 A; 128/328
[58] Field of Search ............. 128/328, 24 A; 367/163, 367/174, 175, 156, 168; 181/400, 401, 167, 168, 0.5, 142; 179/181 R, 115 R, 115.5 R, 115.5 ES, 115.5 PV, 115.5 VC; 340/384, 385, 388

[56] References Cited

U.S. PATENT DOCUMENTS

| | | | |
|---|---|---|---|
| 1,001,968 | 8/1911 | Massey | 181/168 |
| 1,634,292 | 7/1927 | Lederer | 179/181 X |
| 2,411,865 | 12/1946 | Bostwick et al. | 177/386 |
| 3,189,767 | 6/1965 | Goldman et al. | 310/8.2 |
| 4,135,601 | 1/1979 | Tsukagoshi et al. | 181/167 |
| 4,344,503 | 8/1982 | Makamura et al. | 181/168 X |

FOREIGN PATENT DOCUMENTS

| | | |
|---|---|---|
| 0045412 | 2/1982 | European Pat. Off. . |
| 1191720 | 4/1965 | Fed. Rep. of Germany . |
| 3312014 | 10/1984 | Fed. Rep. of Germany . |

*Primary Examiner*—Michael H. Thaler
*Attorney, Agent, or Firm*—Mark H. Jay

[57] ABSTRACT

A shock wave tube has a coil carrier, an isolating foil, and a diaphragm. The diaphragm is made of a bronze alloy, preferably beryllium bronze. The diaphragm is silvered on the side facing the coil carrier. The coil carrier is made of an aluminum oxide ceramic. Advantages deriving from the use of the materials are long life, substantially constant technical parameters and good reproducability of the shock waves generated.

10 Claims, 1 Drawing Sheet

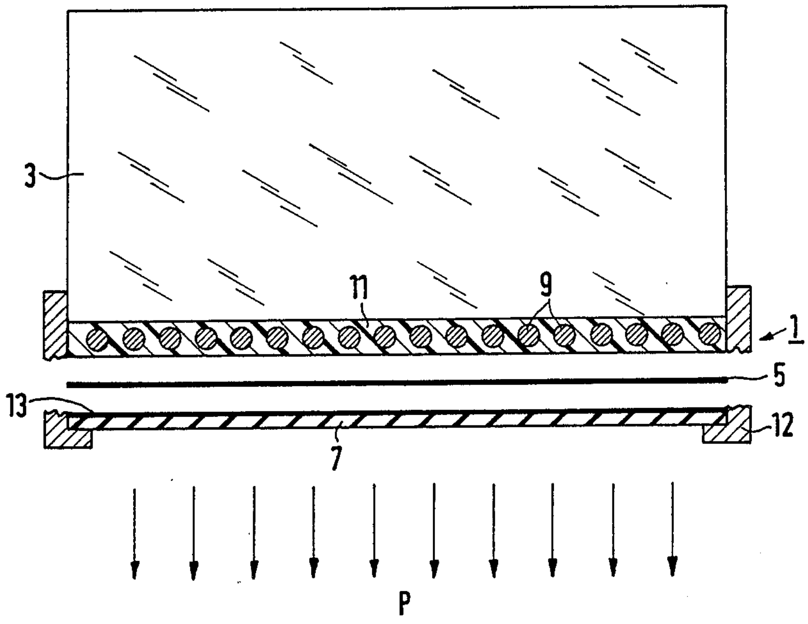
3
11
9
1
5
13
12
7
P

SHOCK WAVE TUBE WITH LONG SERVICE LIFE

CROSS-REFERENCE TO RELATED APPLICATION

This is a continuation of Ser. No. 821,085 filed Jan. 21, 1986, now abandoned.

BACKGROUND OF THE INVENTION

The invention relates to a shock wave tube of the type used for example to shatter kidney stones in a patient.

Shock wave tubes of this type are known. German Offenlegungsschrift 33 12 014 describes such a shock wave tube. Because of the strong (e.g. 100 bar) pressure pulses delivered, the materials of such a shock wave tube are heavily stressed as a result of successive discharges and shock wave emissions. In particular, the discharge coil (which is designed as a disk coil) and the membrane are subject to early material fatigue. In DE-OS 33 12 014 the metal membrane is circumferentially symmetrical and is provided with differing effective cross-sections in order to increase its lifespan. In addition it is indicated that service life is prolonged if pressure is employed to hold the diaphragm against the disc coil.

A shock-wave tube of the type considered herein is also described in commonly owned patent application Ser. No. 634,021, filed 07/24/1984 and entitled "Apparatus for the Contact-Free Disintegration of Calculi", the disclosure of which application is incorporated herein by reference.

One object of the invention is to provide a shock wave tube that will survive many shock wave emissions.

Another object is, in general, to improve on the prior art.

SUMMARY OF THE INVENTION

In accordance with the invention, the coil carrier is composed of aluminum oxide ceramic.

In accordance with the invention, the diaphragm is composed of a bronze alloy or of molybdenum.

The invention provides good and stable radiation levels and long service life of the shock wave tube. Over 3000 shock waves were derived from an aluminum oxide coil carrier without breakage of the coil carrier or high voltage arc-over between the windings of the coil. With a diaphragms composed of the bronze alloy over 3000 shock waves were generated without visual distortion of the diaphragm or evidence of fracture. Wrinkling after a large number of shocks, as otherwise observed with copper, aluminum or steel diaphragms, was therefore absent.

It is especially advantageous for the diaphragm to include a precious metal. A silver layer of about 50 μm improves the shock wave form and the pressure amplitude.

BRIEF DESCRIPTION OF THE DRAWING

The exemplary and non-limiting FIGURE schematically shows a preferred embodiment of the invention.

DETAILED DESCRIPTION OF A PREFERRED EMBODIMENT

In the FIGURE (which is not to scale), 1 generally indicates a shock wave tube, having a coil carrier 3, an insulating foil 5, and a round diaphragm 7 of electrically conducting material. A disc coil designed as a discharge coil 9 is bonded to the front side of the coil carrier as by a synthetic resin 11. The components 9, 5, and 7 are held and tightly pressed together by means of a retaining ring 12 which is fastened to the coil carrier 3 in a suitable manner.

During the operation of the shock tube 1 a short high amplitude electrical voltage pulse is applied to the disc coil 9. The resulting electromagnetic field causes the diaphragm 7 to be repelled from the disc coil 9. The diaphragm 7 is however pressed tightly along its circumference to the disc coil through the intermediate insulating foil 5. In the ideal case the repulsion will be nearly evenly produced over the free surface of the diaphragm 7 and through this a shock wave P will be transmitted. After a number of shock wave emissions the diaphragm 7 will become fatigued. To generate an effective shock wave the diaphragm 7 should advantageously be made of a material having a high conductivity. For reasons of good stability and non-deformability during the generation of a large number of shock waves, the diaphragm 7 should also advantageously consist of a working material of high tensile strength and an elastic modulus greater than 110 KN/mm$^2$. The diaphragm 7 is advantageously made of a bronze alloy, more particularly of a beryllium bronze. The use of a bronze alloy with additions of tin or silver has also been found advantageous. Molybdenum may be alternatively used as material for the diaphragm 7.

The electrical conductivity of the diaphragm 7, and thereby the deflection efficiency during the production of shock waves, may be further improved if the surface of the diaphragm 7 facing the disc coil is coated with a metal, preferably a noble metal. In this connection it has been found to be advantageous to employ a silver layer 13 of about 50 μm. The pressure amplitude has been found to be measurably higher than without the layer.

Since the force of repulsion between the disc coil 9 and the diaphragm 7 should advantageously be directed exclusively in the direction of the column of the shock wave P, the coil carrier 3 should be made from an acoustically stiff material. Ceramic materials have been found well suited for this purpose, and aluminum oxide ceramic of the DIN Class KER 710 has produced especially outstanding results.

Tests of the preferred embodiment have shown that after 3000 shock wave emissions P there is no indication of deformations in the diaphragm 7, such as compression set or relaxation. Also no voltage arc-overs in the synthetic resin encapsulated coil 9 were observed.

Those skilled in the art will understand that changes can be made in the preferred embodiments here described, and that these embodiments can be used for other purposes. Such changes and uses are within the scope of the invention, which is limited only by the claims which follow.

What is claimed is:

1. A shock wave tube of the type which is used to destroy kidney stones and the like in vivo, comprising:

(a) a coil;

(b) a coil carrier of aluminum oxide ceramic; and (c) a diaphragm of a material which is selected from a class containing as members bronze alloys and molybdenum.

2. An improvement to a shock wave tube of the type which is used to destroy kidney stones and the like in vivo and which includes a coil, a coil carrier which carries the coil, and a diaphragm which is located in front of the coil and which produces shock waves in response to energizations and deenergizations of the coil, comprising a coil carrier of aluminum oxide ceramic.

3. The improvement of claim 2, wherein the aluminum oxide ceramic is of the DIN 710 class.

4. An improvement to a shock wave tube of the type which is used to destroy kidney stones and the like in vivo and which includes a coil and a diaphragm which is located in front of the coil and which produces shock waves in response to energizations and deenergizations of the coil, comprising a diaphragm of a material which is selected from a class containing the following members:

(a) bronze alloys; and (b) molybdenum.

5. The improvement of claim 4, wherein the diaphragm is of a material which is selected from a class containing the following members:

(a) tin bronze;

(b) silver bronze; and (c) beryllium bronze.

6. The improvement of claim 4, wherein the diaphragm is coated with a metal.

7. The improvement of claim 6, wherein the metal is coated on that surface of the diaphragm which faces the coil.

8. A shock wave tube of the type which is used to destroy kidney stones and the like in vivo, comprising:

(a) a coil;

(b) a coil carrier of aluminum oxide ceramic of the DIN 710 class; and (c) a diaphragm of tin bronze, silver bronze or beryllium bronze and which is coated with 50 μm of silver on that side which faces the coil.

9. An improvement to a shock wave tube of the type which is used to destroy kidney stones and the like in vivo and which includes a coil and a diaphragm which is located in front of the coil and which produces shock waves in response to energizations and deenergizations of the coil, comprising a diaphragm of a material which is coated with silver and is selected from a class containing the following members:

(a) bronze alloys; and (b) molybdenum.

10. The improvement of claim 1, wherein the metal is approximately 50 μm thick.

* * * * *